United States Patent
Patel et al.

(10) Patent No.: US 10,137,448 B2
(45) Date of Patent: Nov. 27, 2018

(54) MICROFLUIDIC CHIP WITH COATING TO REDUCE FLUID DIFFUSION AND METHOD OF MANUFACTURING SAME

(71) Applicant: FluxErgy, LLC, Irvine, CA (US)

(72) Inventors: Tej Rushikesh Patel, Aliso Viejo, CA (US); Ryan Alan Revilla, Downey, CA (US); Matthew D'Ooge, Irvine, CA (US)

(73) Assignee: FluxErgy, LLC, Irvine, CA (US)

(*) Notice: Subject to any disclaimer, the term of this patent is extended or adjusted under 35 U.S.C. 154(b) by 35 days.

(21) Appl. No.: 15/492,585

(22) Filed: Apr. 20, 2017

(65) Prior Publication Data

US 2017/0216839 A1   Aug. 3, 2017

Related U.S. Application Data

(63) Continuation of application No. 14/934,794, filed on Nov. 6, 2015, now Pat. No. 9,636,674, which is a (Continued)

(51) Int. Cl.
   *B01L 3/00* (2006.01)
   *B01L 7/00* (2006.01)
   (Continued)

(52) U.S. Cl.
   CPC ....... *B01L 3/502707* (2013.01); *B01L 3/5027* (2013.01); *B01L 3/502715* (2013.01); *B01L 7/525* (2013.01); *B32B 37/16* (2013.01); *B32B 38/08* (2013.01); *B32B 38/10* (2013.01); *C12Q 1/6806* (2013.01); *G01N 21/0332* (2013.01);
   (Continued)

(58) Field of Classification Search
   CPC .......... B01L 2200/027; B01L 2200/10; B01L 2200/12; B01L 2300/0654; B01L 2300/0663; B01L 2300/0816; B01L 2300/0883; B01L 2300/0887; B01L 2300/12; B01L 2300/123; B01L 2300/168; B01L 2300/18; B01L 2300/1827; B01L 3/5027; B01L 3/502707; B01L 3/50851; B01L 3/50853; B01L 7/525; B01L 2200/0689; B01L 2200/028; B32B 2307/202; B32B 2383/00; B32B 2457/00; B32B 37/12; B32B 37/16; B32B 38/08; B32B 38/10; C12Q 1/6806; G01N 2021/056; G01N 2021/058;
   (Continued)

(56) References Cited

U.S. PATENT DOCUMENTS

2004/0156753 A1* 8/2004 Roitman ............. B01J 19/0093
                                                              422/504
2005/0272142 A1* 12/2005 Horita ............... B01L 3/502707
                                                              435/287.1
(Continued)

*Primary Examiner* — Jennifer Wecker
(74) *Attorney, Agent, or Firm* — K&L Gates LLP; Louis C. Cullman; Joseph F. Arand

(57) ABSTRACT

A microfluidic chip is disclosed herein. In an embodiment, the microfluidic chip includes a body including at least one microfluidic pathway configured to receive a fluid sample, the at least one microfluidic pathway including a coating configured to reduce fluid diffusion and seal a surface of the at least one microfluidic pathway, and a heating device located on the body and forming a heating zone within a portion of the at least one microfluidic pathway.

20 Claims, 6 Drawing Sheets

Related U.S. Application Data continuation of application No. 14/028,320, filed on Sep. 16, 2013, now Pat. No. 9,180,652.

(51) Int. Cl.

| | |
|---|---|
| *G01N 21/00* | (2006.01) |
| *G01N 21/27* | (2006.01) |
| *B32B 38/10* | (2006.01) |
| *B32B 37/16* | (2006.01) |
| *B32B 38/08* | (2006.01) |
| *C12Q 1/6806* | (2018.01) |
| *G01N 21/03* | (2006.01) |
| *G01N 21/05* | (2006.01) |
| G01N 15/14 | (2006.01) |
| B32B 37/12 | (2006.01) |
| G01N 27/447 | (2006.01) |
| G01N 35/00 | (2006.01) |
| G01N 21/64 | (2006.01) |

(52) U.S. Cl.
CPC .......... *G01N 21/05* (2013.01); *G01N 21/272* (2013.01); *B01L 3/50851* (2013.01); *B01L 3/50853* (2013.01); *B01L 2200/027* (2013.01); *B01L 2200/028* (2013.01); *B01L 2200/0689* (2013.01); *B01L 2200/10* (2013.01); *B01L 2200/12* (2013.01); *B01L 2300/0654* (2013.01); *B01L 2300/0663* (2013.01); *B01L 2300/0816* (2013.01); *B01L 2300/0883* (2013.01); *B01L 2300/0887* (2013.01); *B01L 2300/12* (2013.01); *B01L 2300/123* (2013.01); *B01L 2300/168* (2013.01); *B01L 2300/18* (2013.01); *B01L 2300/1827* (2013.01); *B32B 37/12* (2013.01); *B32B 2307/202* (2013.01); *B32B 2383/00* (2013.01); *B32B 2457/00* (2013.01); *G01N 27/44791* (2013.01); *G01N 2021/056* (2013.01); *G01N 2021/058* (2013.01); *G01N 2021/6482* (2013.01); *G01N 2035/00158* (2013.01)

(58) Field of Classification Search
CPC ....... G01N 2021/6482; G01N 21/0332; G01N 21/05; G01N 27/44791; G01N 2035/00158

See application file for complete search history.

(56) References Cited

U.S. PATENT DOCUMENTS

| | | | |
|---|---|---|---|
| 2008/0199362 A1* | 8/2008 | Chong | ........... B01F 5/0603 422/400 |
| 2011/0028293 A1* | 2/2011 | Atkin | ........... B01L 3/502707 493/374 |

* cited by examiner

MICROFLUIDIC CHIP WITH COATING TO REDUCE FLUID DIFFUSION AND METHOD OF MANUFACTURING SAME

CROSS REFERENCE TO RELATED APPLICATION

The present application is a continuation of U.S. patent application Ser. No. 14/934,794, entitled "Microfluidic Chips with Optically Transparent Glue Coating and a Method of Manufacturing Microfluidic Chips with Optically Transparent Glue Coating for a Microfluidic Device," filed Nov. 6, 2015, which is a continuation of U.S. patent application Ser. No. 14/028,320, entitled "Microfluidic Chips with Optically Transparent Glue Coating and a Method of Manufacturing Microfluidic Chips with Optically Transparent Glue Coating for a Microfluidic Device," filed Sep. 16, 2013, now U.S. Pat. No. 9,180,652, the entire contents of each of which is hereby incorporated by reference herein.

BACKGROUND OF THE DISCLOSURE

Field of Disclosure

The present disclosure relates generally to a method of manufacturing microfluidic chips for handling fluid samples on a microfluidic level, and, more specifically, to a method of manufacturing microfluidic chips with coating to reduce fluid diffusion and microfluidic chips with a coating to reduce fluid diffusion. The manufactured microfluidic chips can be used to perform real-time analysis, for example, polymerase chain reaction (PCR) analysis.

Discussion of the Related Art

Microfluidics can be used in medicine or cell biology researches and refers to the technology that relates to the flow of liquid in channels of micrometer size. At least one dimension of the channel is of the order of a micrometer or tens of micrometers to be considered as microfluidics. In particular, microfluidic devices are useful for manipulating or analyzing micro-sized fluid samples on microfluidic chips, with the fluid samples typically in extremely small volumes down to less than picoliters.

When manipulating or analyzing fluid samples, fluids are pumped onto the micro-channel of microfluidic chips in doses or are continuously flowed onto the micro-channel of microfluidic chips. If the fluid sample is pumped in doses, the fluid sample stays in the micro-channel of the microfluidic chip until the fluid sample is suctioned out from the micro-channel. The fluid sample can be manipulated or analyzed while being held in the micro-channel.

Alternatively, for continuous flow analysis, the fluid is pumped continuously into the micro-channel. Due to the continuous fluid pumping, the fluid sample instead flows and travels through the micro-channel and exits the micro-channel when reaches the outlet of the micro-channel. The fluid sample can be manipulated or analyzed while flowing through the micro-channel, and one can perform a biochemical reaction examination on the continuously flowing fluid sample, including treating and manipulating processes of the fluid.

Presently, microfluidic chips have micro-channels molded in PolyDiMethyiSiloxane ("PDMS"). The micro-channels then are sealed when the PDMS block is bonded to a glass slide.

FIGS. IA-1D are perspective views of manufacturing a microfluidic chip mold according to the related art. The manufacturing of a microfluidic chip according to the related art takes a channel design and duplicates the channel design onto a photomask 10. As shown in Figure IA, a photoresist 22 is deposited onto a semiconductor wafer 20. As shown in FIG. 1B, the photomask 10 that reflects the channel design 12 is placed over the wafer 20, and the wafer 20 with the mask 10 undergoes UV exposition to cure the photoresist 22. Then, as shown in FIG. 10, the wafer 20 with the cured photoresist 22' is developed. The 'negative' image of a channel according to the channel design is etched away from the semiconductor wafer 20. As shown in FIG. 1D, after all residual photoresist are removed, the resulting wafer becomes a mold 20' that provides the channel according to the channel design 12'.

FIG. 2 are perspective views of the steps of manufacturing a microfluidic chip according to the related art. As shown in FIG. 2, PDMS in liquid form 30 is poured onto the mold 20'. Liquid PDMS 30 may be mixed with crosslinking agent. The mold 20' with liquid PDMS 30 is then placed into a furnace to harden PDMS 30. As PDMS is hardened, the hardened PDMS block 30' duplicates the micro-channel 12" according to the channel design. The PDMS block 30' then may be separated from the mold 20'. To allow injection of fluid into the micro-channel 12" (which will subsequently be sealed), inlet or outlet is then made in the PDMS block 30' by drilling into the PDMS block 30' using a needle. Then, the face of the PDMS block 30' with micro-channels and a glass slide 32 are treated with plasma. Due to the plasma treatment, the PDMS block 30' and the glass slide 32 can bond with one another and close the chip.

The microfluidic chip according to the related all has a micro-channel in the PDMS block. PDMS belongs to a group of polymeric organosilicon compounds that are commonly referred to as silicone, and can be deposited onto the master mold in liquid form and subsequently hardened.

However, PDMS is inherently porous and due to its polymer structure, PDMS is highly permeable. Thus, diffusion of fluid sample through PDMS has been observed. Such diffusion of fluid sample does not impact a microfluidic system that pumps fluid samples in doses as significantly as a continuous flow microfluidic system. In particular, when a continuous flow microfluidic system monitors treating and manipulating of the flowing fluid in real-time analysis applications, diffusion or unaccounted loss of fluid sample can significantly impact the real-time analysis. Thus, there exists a need for reducing diffusion or loss of fluid sample in micro-channel of a microfluidic chip.

SUMMARY OF THE DISCLOSURE

Accordingly, embodiments of the present disclosure are directed to a method of manufacturing microfluidic chips for handling fluid samples on a microfluidic level and microfluidic chips that can substantially obviate one or more of the problems due to limitations and disadvantages of the related art.

An object of embodiments of the present disclosure is to provide a method of manufacturing microfluidic chips to reduce fluid diffusion in micro-channel, and microfluidic chips manufactured using the same.

An object of embodiments of the present disclosure is to provide a method, of manufacturing microfluidic chips with micro-channel coating, and microfluidic chips manufactured using the same.

Additional features and advantages of embodiments of the present disclosure will be set forth in the description which follows, and in part will be apparent from the description, or may be learned by practice of embodiments of the present disclosure. The objectives and other advantages of the embodiments of the present disclosure will be realized and attained by the structure particularly pointed out in the written description and claims hereof as well as the appended drawings.

To achieve these and other advantages and in accordance with the purpose of embodiments of the present disclosure, as embodied and broadly described, a microfluidic chip device according to an embodiment of the present disclosure includes a substrate having a first thickness, at least one microfluidic pathway in the substrate, a coating along the microfluidic pathway, and a glass layer having a second thickness on the substrate and above the microfluidic pathway, wherein the coating contains cyanoacrylates, and the first thickness is greater than the second thickness.

In accordance with another embodiment of the present disclosure, as embodied and broadly described, a microfluidic chip device includes a substrate having a first thickness, at least one microfluidic pathway in the substrate, a coating along the microfluidic pathway, and a glass layer having a second thickness on the substrate and above the microfluidic pathway, wherein the coating contains an optically transparent material, and the first thickness is greater than the second thickness.

In accordance with another embodiment of the present disclosure, as embodied and broadly described, a method for manufacturing a microfluidic chip device includes etching a substrate having a first thickness for forming at least one microfluidic pathway in the substrate, coating the substrate, and bonding a glass layer having a second thickness on the substrate and above the microfluidic pathway, wherein the step of coating includes coating an optically transparent material, and the first thickness is greater than the second thickness.

In accordance with another embodiment of the present disclosure, as embodied and broadly described, a microfluidic chip device includes a coating along the microfluidic pathway, wherein the coating includes cyanoacrylates, an UV curable epoxy adhesive, a gel epoxy or epoxy under trade name of EPO-TEK OG175, MasterBond EP30LV-1 or Locite 0151.

In accordance with another embodiment of the present disclosure, as embodied and broadly described, a method for manufacturing a microfluidic chip device includes etching a substrate having a first thickness for forming at least one microfluidic pathway in the substrate and coating along the microfluidic pathway, wherein the coating includes coating with cyanoacrylates, an UV curable epoxy adhesive, a gel epoxy or epoxy under trade name of EPO-TEK OG1.75, MasterBond EP30LV-1 or Locite 0151.

It is to be understood that both the foregoing general description and the following detailed description are exemplary and explanatory and are intended to provide further explanation of embodiments of the present disclosure as claimed.

BRIEF DESCRIPTION OF THE DRAWINGS

The accompanying drawings, which are included to provide a further understanding of embodiments of the present disclosure and are incorporated in and constitute a part of this specification, illustrate embodiments of the present disclosure and together with the description serve to explain the principles of embodiments of the present disclosure.

DETAILED DESCRIPTION OF THE PREFERRED EMBODIMENTS

Reference will now be made in detail to the preferred embodiments of the present disclosure, examples of which are illustrated in the accompanying drawings.

Figure 1A:
FIGS. 1A-1D are perspective views of manufacturing a microfluidic chip mold according to the related art.
Figure 1B:
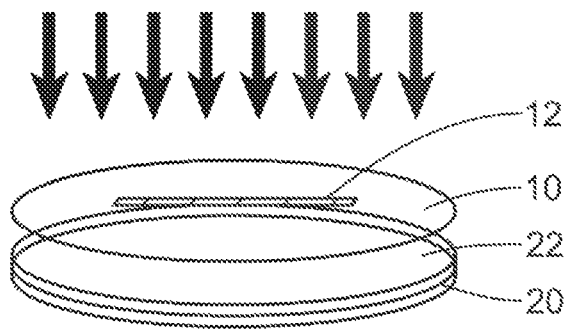
Figure 1C:
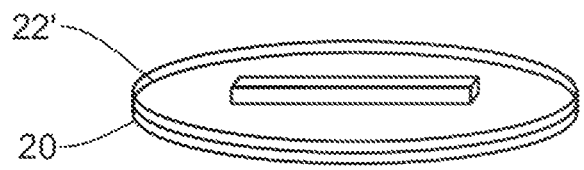
Figure 1D:
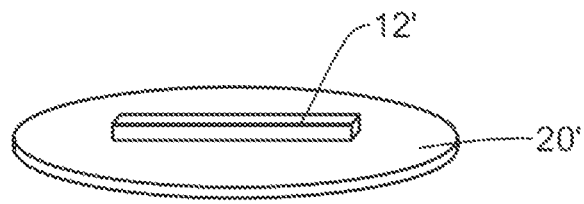
Figure 2:
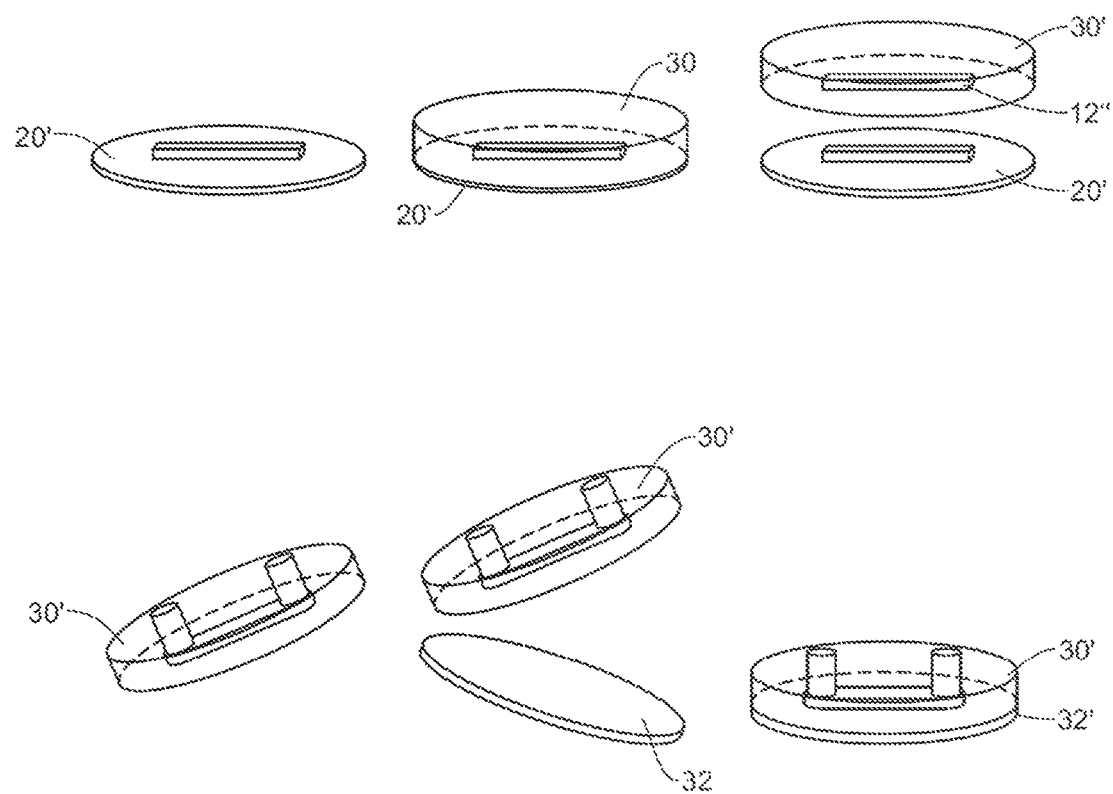
FIG. 2 illustrates the steps of manufacturing a microfluidic chip according to the related art.
Figure 3:
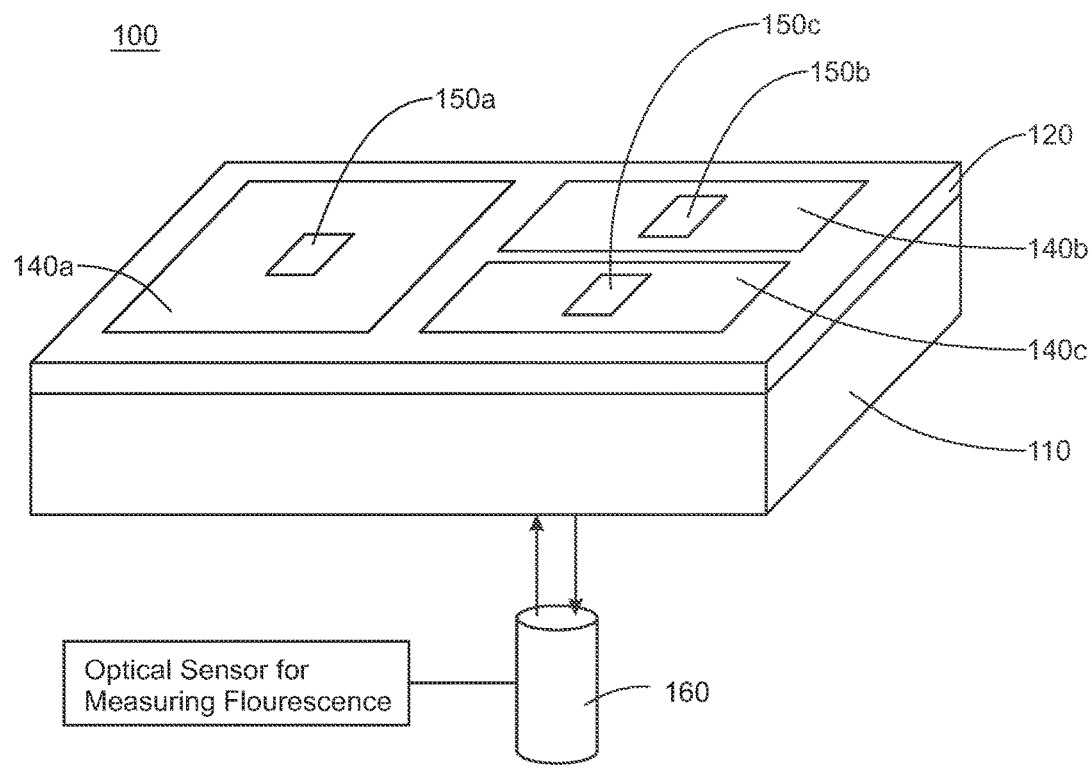
FIG. 3 is a perspective view of a microfluidic chip for a microfluidic system according to an embodiment of the present disclosure.
Figure 4:
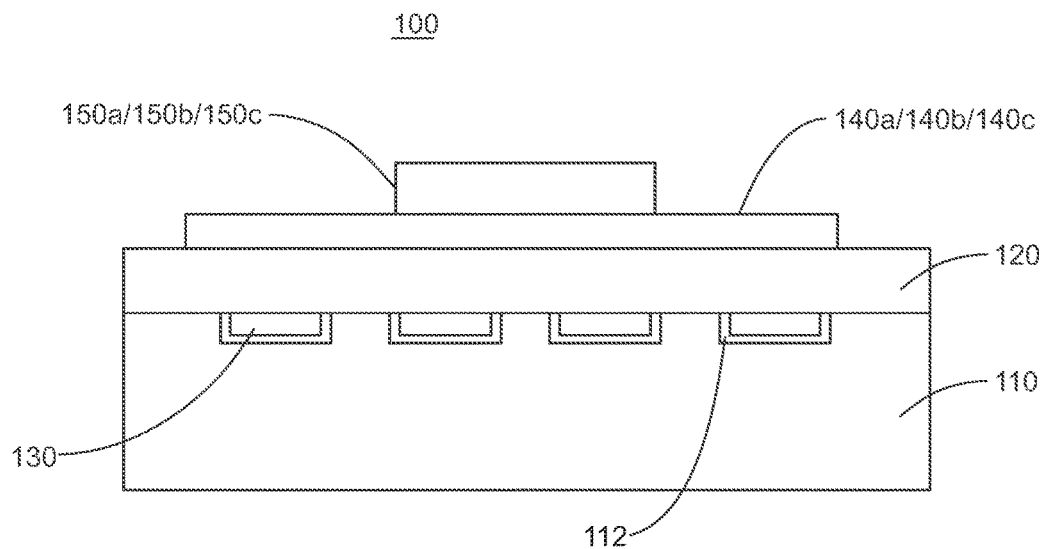
FIG. 4 is a side view of the microfluidic chip shown in FIG. 3.

FIG. 3 is a perspective view of a microfluidic chip for a microfluidic system according to an embodiment of the present disclosure, and FIG. 4 is a side view of the microfluidic chip shown in FIG. 3. As shown in FIGS. 3 and 4, a microfluidic chip 100 includes a PDMS substrate 110 and a glass layer 120 on the substrate 110. The glass layer 120 may be formed of borosilicate. As shown in the substrate 110. For instance, the glass layer 120 may have a thickness of about 0.01 inch or less.

The substrate 110 includes micro-channels 130. The micro-channels 130 form a microfluidic pathway, and the channels allow fluid samples to be flowed through therein. The micro-channels 130 may be formed by etching the substrate 110.

After the micro-channels 130 are formed in the substrate 110 but prior to sealing micro-channels 130 with the glass layer 120, the substrate 110 is coated with cyanoacrylates 112 to seal the surface pores of the substrate 110. Cyanoacrylates are acylic resin and are mainly used as adhesives. However, cyanoacrylates are not used as adhesives in the micro-channels of the substrate 110. Instead, cyanoacrylates are allowed to set to form a coating along the micro-channels 130.

When coating the substrate 110, the amount of cyanoacrylates deposited is controlled so as not to fill the micro-channels 130 of the substrate 110. In addition or alternatively, the micro-channels 130 are formed wider and/or deeper in the substrate 110 to account for the subsequent coating thickness of cyanoacrylates 112.

The microfluidic chip 100 further includes heaters 140a, 140b and 140c. For example, the heaters 140a, 140b and 140c may be resistive heating devices, such as thin-film heaters. The heaters 140a, 140b and 140c may be formed by applying a thin film of conductive material directly on the glass layer 120. For example, the heaters 140a, 140b and 140c may include aluminum. More specifically, the heaters 140a, 140b and 140c may have a thickness of about 0.001 inch or less.

The microfluidic chip 100 further includes temperature sensors 150a, 150b and 150c. For example, the temperature sensors 150a, 150b and 150c may be resistance temperature detectors. The temperature sensors 150a, 150b and 150c provide real-time temperature detection to more than one zones or portions of the microfluidic chip 100. The real-time temperature detection is then used to control heaters 140a, 140b and 140c, respectively. As such, the microfluidic chip 100 may have independently-temperature-controlled zones.

A microprocessor (not shown) may be connected to the temperature sensors 150a, 150b and 150c and the heaters 140a, 140b and 140c to provide independently-temperaturecontrolled zones for the microfluidic chip 100. For example, the microprocessor may implement a control algorithm, such as PID control to receive temperature inputs from the temperature sensors 150a, 150b and 150c and dynamically controls the output of the heaters 140a, 140b and 140c.

For real-time analysis, an optical sensor 160 is further included and can be placed above or below the microfluidic chip 100. The optical sensor 160 provides real-time monitoring of the manipulation of the fluid sample in the micro-channel 130 of the microfluidic chip 100. The same microprocessor (not shown) can also receive and control the optical sensor 160.

Figure 5:
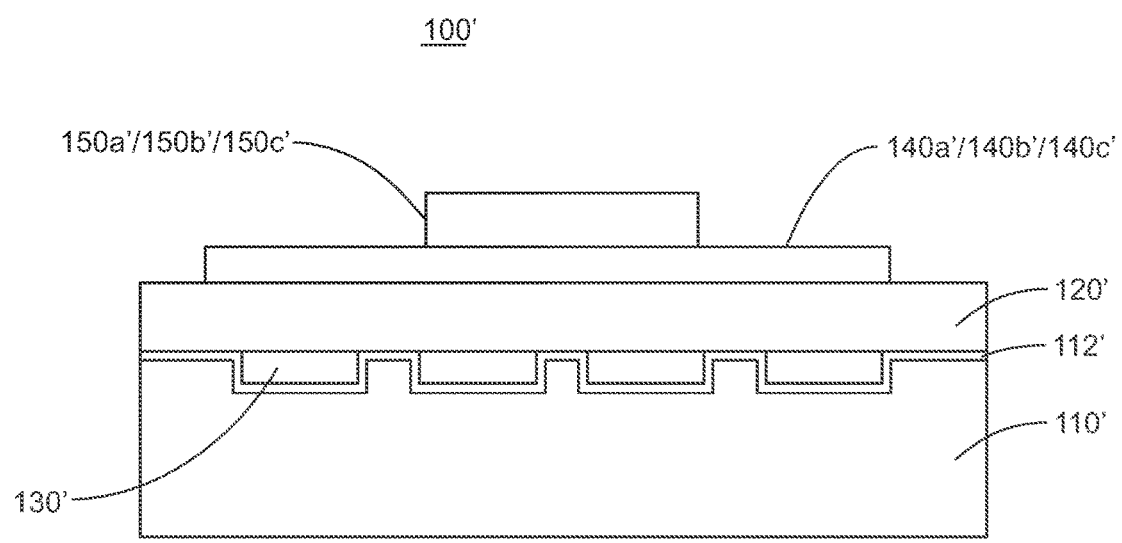
FIG. 5 is a side view of the microfluidic chip according to another embodiment of the present disclosure.

FIG. 5 is a side view of the microfluidic chip according to another embodiment of the present disclosure. In FIG. 5, a microfluidic chip 100' includes a layer of cured optically transparent material 112' between a substrate 110' and a seal layer 120'. As shown in FIG. 3, the thickness of the seal layer 120' is much smaller than the thickness of the substrate 110'. For instance, the seal layer 120' may have a thickness of about 0.01 inch or, less.

The substrate 110' includes micro-channels 130'. The micro-channels 130' form a microfluidic pathway, and the channels allow fluid samples to be flowed through therein. The micro-channels 130' may be formed by etching the substrate 110'.

After the micro-channels 130' are formed in the substrate 110' but prior to sealing micro-channels 130' with the seal layer 120', the substrate 110' is coated with an optically transparent material to seal the surface of the substrate 110'. The optically transparent material is allowed to set or hardened to form the layer of cured optically transparent material 112'. An UV curable epoxy adhesive, a gel epoxy or epoxy under trade name of EPO-TEK OG175, MasterBond EP30LV-1 or Locite 0151 may be used to coat the surface of the substrate 110'.

When coating the substrate 110', the amount of the optically transparent material deposited are controlled so as not to fill the micro-channels 130' of the substrate 110'. In addition or alternatively, the micro-channels 130' are formed wider and/or deeper in the substrate 110' to account for the subsequent layer of cured optically transparent material 112'.

The microfluidic chip 100' further includes heaters 140a', 140b' and 140c'. For example, the heaters 140a', 140b' and 140c' may be resistive heating devices, such as thin-film heaters. The heaters 140a', 140b' and 140c' may be formed by applying a thin film of conductive material directly on the seal layer 120'. For example, the heaters 140a', 140b' and 140c' may include aluminum. More specifically, the heaters 140a', 140b' and 140c' may have a thickness of about 0.001 inch or less.

The microfluidic chip 100' further includes temperature sensors 150a', and 150c'. For example, the temperature sensors 150a', 150b' and 150c' may be resistance temperature detectors. The temperature sensors 150a', 150b' and provide real-time temperature detection to more than one zones or portions of the microfluidic chip 100'. The real-time temperature detection is then used to control heaters 140a', 140b' and 140c', respectively. As such, the microfluidic chip 100 may have independently-temperature-controlled zones.

A microprocessor (not shown) may be connected to the temperature sensors 150a', 150b' and 150c' and the heaters 140a', 140b' and 140c' to provide independently-temperature-controlled zones for the microfluidic chip 100'. For example, the microprocessor may implement a control algorithm, such as PID control to receive temperature inputs from the temperature sensors 150a', 150b' and 150c' and dynamically controls the output of the heaters 140a', 140b' and 140c'.

Although not shown, for real-time analysis, an optical sensor is further included and can be placed above or below the microfluidic chip 100'. The optical sensor provides real-time monitoring of the manipulation of the fluid sample in the micro-channel 130' of the microfluidic chip 100'. The optical sensor may be controlled by a microprocessor.

Figure 6:
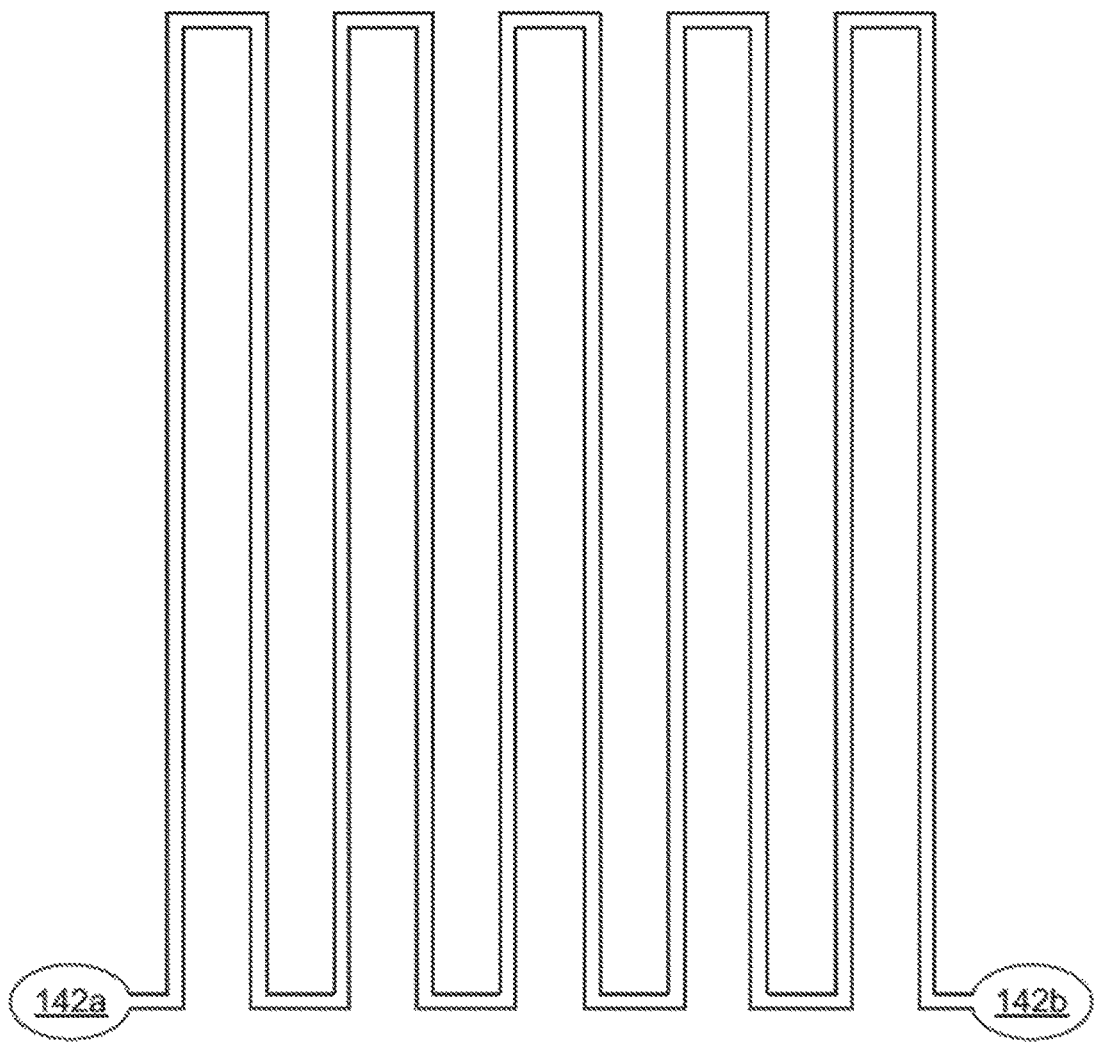
FIG. 6 is a top view of a heater for a microfluidic chip of a microfluidic system according to an embodiment of the present disclosure.

FIG. 6 is a top view of a heater for a microfluidic chip of a continuous-flow microfluidic system according to an embodiment of the present disclosure. As shown in FIG. 6, a thin-film heater 140 for a microfluidic chip of a microfluidic system preferably may include two electrical interface pads 142a and 142b. The two electrical interface pads 142a and 142b may receive voltage and/or current. More specifically, electrical resistance or heat may be generated by the thin-film heater 140 based on $V^2/R$ or $I^2 \times R$. Such heat may provide temperature to the channels 130 or 130' shown in FIG. 4 or 5.

Preferably, the thin-film heater 140 is spread above the channels 130 or 130' evenly to provide consistent heating of the channel below. The thin-film heater 140 may have a line-like shape between the two electrical interface pads 142a and 142b. For example, the thin-film heater 140 may have elongated strips that are substantially parallel with one another.

It will be apparent to those skilled in the art that various modifications and variations can be made in the microfluidic chip of embodiments of the present disclosure without departing from the spirit or scope of the present disclosure. Thus, it is intended that embodiments of the present disclosure cover the modifications and variations of this disclosure provided they come within the scope of the appended claims and their equivalents.

What is claimed:

1. A microfluidic chip comprising:
a body including at least one microfluidic pathway configured to receive a fluid sample, the at least one microfluidic pathway including a coating configured to reduce fluid diffusion and seal a surface of the at least one microfluidic pathway; and
a heating device located on the body and forming a heating zone within a portion of the at least one microfluidic pathway.

2. The microfluidic chip of claim 1, wherein the body includes at least two layers, the at least one microfluidic pathway formed between the at least two layers.

3. The microfluidic chip of claim 1, wherein the body is formed of multiple layers, the at least one microfluidic pathway formed on a first side of a first layer of the multiple layers, the heating device located on an opposite second side of the first layer.

4. The microfluidic chip of claim 3, wherein the heating device includes a layer of conductive material applied to the second side of the first layer.

5. The microfluidic chip of claim 3, wherein at least a portion of the at least one microchannel is etched into a second layer attached to the first side of the first layer.

6. The microfluidic chip of claim 1, wherein the heating device includes a resistive heating device.

7. The microfluidic chip of claim 1, wherein the heating device includes a layer of conductive material applied to an outer surface of the body.

8. The microfluidic chip of claim 1, which includes a plurality of heating devices forming a plurality of independent heating zones within separate portions of the at least one microchannel.

9. The microfluidic chip of claim 1, wherein the heating device is configured to be connected to a microprocessor to enable the microprocessor to control the temperature of the fluid sample within the at least one microfluidic pathway by controlling the heating device.

10. The microfluidic chip of claim 9, wherein the microprocessor further controls an optical device to perform an optical analysis of the fluid sample.

11. A microfluidic system comprising:
a microfluidic chip including a first side and a second side, the microfluidic chip including at least one microfluidic pathway for a fluid sample to flow through, the at least one microfluidic pathway including a coating configured to reduce fluid diffusion and seal a surface of the at least one microfluidic pathway; and
a microprocessor configured to cause (i) the fluid sample within the at least one microfluidic pathway to be heated from the first side of the microfluidic chip, and (ii) the fluid sample within the at least one microfluidic pathway to be optically analyzed from the second side of the microfluidic chip.

12. The microfluidic system of claim 11, which includes a heating device on the first side of the microfluidic chip, the heating device configured to be connected to the microprocessor.

13. The microfluidic system of claim 12, wherein the heating device is part of the microfluidic chip.

14. The microfluidic system of claim 13, wherein the heating device includes a layer of conductive material applied to the first side of the microfluidic chip.

15. The microfluidic system of claim 11, wherein the first and second sides of the microfluidic chip are opposite sides of the microfluidic chip.

16. A microfluidic chip comprising:
a body formed of at least a first layer having a first thickness and a second layer having a second thickness, the first thickness greater than the second thickness;
at least one microfluidic pathway etched into the body and configured to receive a fluid sample; and
a coating configured to reduce fluid diffusion and seal a surface of the at least one microfluidic pathway, the coating exposed along the at least one microfluidic pathway to reduce fluid diffusion as the fluid sample flows through the at least one microfluidic pathway.

17. The microfluidic chip of claim 16, wherein the first layer is a same length and width as the second layer.

18. The microfluidic chip of claim 16, wherein the at least one microfluidic pathway is located on a first side of the second layer, and which includes a heating device located on an opposite second side of the second layer.

19. The microfluidic chip of claim 18, wherein the heating device includes a layer of conductive material applied to the second side of the second layer.

20. The microfluidic chip of claim 16, wherein at least the first layer is optically transparent to enable an optical analysis of the fluid sample.

* * * * *